US011878083B2

(12) United States Patent
Ballamy et al.

(10) Patent No.: US 11,878,083 B2
(45) Date of Patent: Jan. 23, 2024

(54) FIBRES, A PROCESS FOR PRODUCING SUCH FIBRES AND A WOUND DRESSING INCORPORATING THEM

(71) Applicant: CONVATEC TECHNOLOGIES INC., Las Vegas, NV (US)

(72) Inventors: Lucy Louisa Ballamy, Llangollen (GB); Sharon Lam Po Tang, Nantwich (GB); Marion Herbe, Morblhan (FR); Alan Rogers, Holywell (GB); Sean Kelly, Deeside (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 17/522,126

(22) Filed: Nov. 9, 2021

(65) Prior Publication Data
US 2022/0096704 A1   Mar. 31, 2022

Related U.S. Application Data

(62) Division of application No. 13/811,483, filed as application No. PCT/GB2011/001102 on Jul. 22, 2011, now abandoned.

(30) Foreign Application Priority Data

Jul. 22, 2010 (GB) ..................................... 1012333

(51) Int. Cl.
| | | |
|---|---|---|
| *A61L 15/22* | (2006.01) | |
| *B29C 48/05* | (2019.01) | |
| *A61L 26/00* | (2006.01) | |
| *D01F 4/00* | (2006.01) | |
| *D01D 5/06* | (2006.01) | |
| *D01F 8/02* | (2006.01) | |
| *B29C 48/88* | (2019.01) | |
| *A61L 15/44* | (2006.01) | |
| *A61L 15/60* | (2006.01) | |
| *B29L 31/00* | (2006.01) | |

(52) U.S. Cl.
CPC ............. *A61L 15/225* (2013.01); *A61L 15/44* (2013.01); *A61L 15/60* (2013.01); *A61L 26/0052* (2013.01); *B29C 48/05* (2019.02); *B29C 48/919* (2019.02); *D01D 5/06* (2013.01); *D01F 4/00* (2013.01); *D01F 8/02* (2013.01); *A61L 2300/232* (2013.01); *A61L 2300/252* (2013.01); *A61L 2300/41* (2013.01); *A61L 2300/412* (2013.01); *A61L 2300/434* (2013.01); *B29K 2005/00* (2013.01); *B29L 2031/731* (2013.01)

(58) Field of Classification Search
CPC .... D01D 5/0007; D01D 5/0015; D01D 5/003; D01D 5/0038; D01D 5/0046; D01D 5/0053; D01D 5/0061; D01D 5/0069; D01D 5/0076; D01D 5/0084; D01D 5/0092; D01D 5/06; A61L 15/225; A61L 15/44; A61L 15/60; A61L 26/0052; A61L 2300/232; A61L 2300/252; A61L 2300/41; A61L 2300/412; A61L 2300/434; B29C 48/05; B29C 48/919; D01F 4/00; D01F 8/02; B29K 2005/00; B29L 2031/731; C08L 89/00; C08L 5/06
See application file for complete search history.

(56) References Cited

U.S. PATENT DOCUMENTS

| | | | | |
|---|---|---|---|---|
| 3,249,109 | A * | 5/1966 | Maeth | A61L 15/44 602/50 |
| 5,871,680 | A * | 2/1999 | Macheras | B01D 67/0016 264/211.13 |
| 6,080,420 | A * | 6/2000 | Qin | D01F 9/04 424/443 |
| 6,140,257 | A * | 10/2000 | Kershaw | A61L 15/225 442/310 |
| 6,793,645 | B2 | 9/2004 | Griffiths et al. | |
| 7,799,261 | B2 * | 9/2010 | Orr | D01D 5/0061 264/441 |
| 2002/0012693 | A1 | 1/2002 | Cohen et al. | |
| 2005/0224999 | A1 * | 10/2005 | Andrady | D01F 11/00 425/72.2 |
| 2006/0142242 | A1 | 6/2006 | Mohajer et al. | |
| 2006/0189516 | A1 | 8/2006 | Yang et al. | |

(Continued)

FOREIGN PATENT DOCUMENTS

| | | |
|---|---|---|
| EP | 1424086 A1 | 6/2004 |
| WO | 9610106 A1 | 4/1996 |
| WO | 9739170 A1 | 10/1997 |

(Continued)

OTHER PUBLICATIONS

Barnea, Yoav et al; "A review of the applications of the hydrofiber dressing with silver (aquacell ag(r)) in wound care." Ther. Clin. Risk Management (2010) 6 p. 21-27.

Zahedi, Payam et al; "A review on wound dressings with an emphasis on electrospun nanofibrous polymeric bandages." Polym. Adv. Technol. (2010) 21 p. 77-95.

Dongowski, Gerhard et al; "The degree of mehtylation influences the degradation of pectin in the intestinal tract of rats and in vitro." J. Nutr. (2002) 132 p. 1935-1944.

Semdé, Rasmane et al; "Synthesis and enzymatic degradation of epichlorohydrin crosslinked pectins." Drug Develop. Ind. Pharmacy (2003) 29(2) p. 203-213.

(Continued)

*Primary Examiner* — Jeffrey M Wollschlager
(74) *Attorney, Agent, or Firm* — Taft Stettinius & Hollister LLP; Ryan O. White; Derek B. Lavender

(57) ABSTRACT

Multi component fibres for the reduction of the damaging activity of wound exudate components such as protein degrading enzymes and inflammatory mediators in wounds, the fibres comprising: from 10% to 100% by weight of the fibres of pectin and a sacrificial proteinaceous material in a weight ratio of 100:0 to 10:90 pectin to sacrificial proteinaceous material and from 0% to 90% by weight of the fibres of another polysaccharide or a water soluble polymer.

18 Claims, 1 Drawing Sheet

(56) References Cited

U.S. PATENT DOCUMENTS

2009/0087469 A1* 4/2009 Zhang .................. A61K 9/0024
514/23
2012/0045487 A1* 2/2012 Lahann .................. A61P 31/10
977/774

FOREIGN PATENT DOCUMENTS

| WO | 0164132 A1 | 9/2001 |
|---|---|---|
| WO | 07137733 A1 | 6/2007 |
| WO | 09068249 A1 | 6/2009 |

OTHER PUBLICATIONS

Pawar, Atmaram et al "effect of core and surface cross-linking on the entrapment of metronidazole in pectin beads." Acta Pharm. (2008) 58 p. 75-85.
Singh, Saranjit et al, "Alteration in dissolution characteristics of gelatin containing formulations." Pharmaceut. Technol. (Apr. 2002) p. 36-58.
Audic, Jean-Luc et al, "Non-food applications of milk components and dairy co-products: a review." Lait (2003) 83 p. 417-438.
Rides, Marin and Allen, Crispin, "Effect of die deometry on shear viscosity and entrance pressure drop determination by capillary extrusion rheometry." NPL report MATC(a)56 (2001).
Fox, Thomas G. and Flory, Paul J.; "Viscosity-molecular weight and viscosity temperature relationships for polystyrene and polyisobutylene." J. Am. Chem. Soc. (1948) 70 (7) p. 2384-2395.
Pamphlet 3005 from the US custom and border patrol "What every member of the trade community should know about: wadding, gauze, bandages, and similar articles." (2006).
Garnier, Catherine et al, "Phase diagrams of pectin-calcium systems: influence of pH, ionic strength, and temperature on the gelation of pectins with different degrees of methylation." Carbo. Res. (1993) 240 p. 219-232.
Sriamornsak, Pornsak; "CHemistry of pectin and its pharmaceutical uses: a review." Silpakorn U. Int. J. (2003) 3(1-2) p. 206-228.
Liao, Ming-Long et al, "Low methoxy pectin of sunflower biomass." 14th Australian Sunflower Association Conference, 2005.
Gaube, Johan et al, "Polydispersity effects in the system poly(ethylene glycol)+ dextran + water." J. Chem. Eng. Data (1993) 38 p. 207-210.
Immergut, Edmund H. and Mark, Herman F.; "Principles of plasticization." Advances. Chem. (1965) p. 1-26.
Shefer, Adi and Gottlieb, Moshe; "Effect of cross-links on the glass transition temperature of end linked elastomers." Macromolecules (1992) 25 p. 4036-4042.
Dupuis, G et al, "Colonic drug delivery: influence of crosslinking agent on pectin beads properties and role of the shell capsule type. "Drug Develop. Indus !. Pharm. (2006) 32 p. 847-855.
Djokić, Stojan, "Synthesis and antimicrobial activity of silver citrate complexes." Bioinorg. Chem. Appl. (2008) article ID 436458.
The Altrafine web page describing guar gum, https://www.altrafine.com/fasthydrationguargumpowder/, downloaded Sep. 18, 2017.
Jayakumar, Gladstone Christopher et al, "Studies on the physiochemical characteristics of collagen-pectin composites." Adv. (2014) 4 p. 63840-63849.
Canadian Patent Application No. 2,806,142 Office Action dated May 12, 2017.
Mexican Patent Application No. MX/a/2013/000895 Office Action dated Apr. 9, 2017.
European Patent Application No. 11746600.3 Communication dated Sep. 14, 2017.
European Examination Report; European Patent Office; European Patent Application No. 11746600.3; dated Mar. 6, 2020; 6 pages.

* cited by examiner

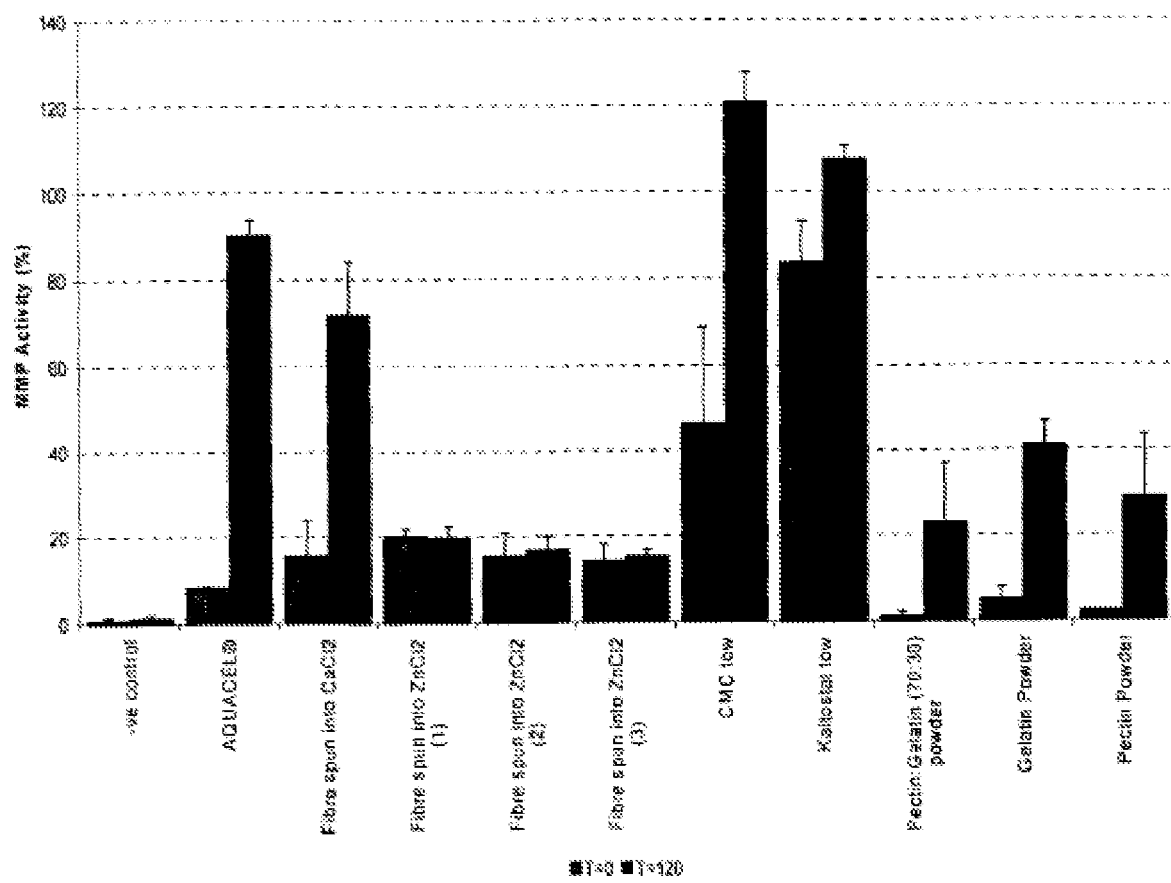
Table 3

FIBRES, A PROCESS FOR PRODUCING SUCH FIBRES AND A WOUND DRESSING INCORPORATING THEM

CROSS-REFERENCE TO RELATED APPLICATION(S)

This application is a divisional application of, and claims the priority benefit of, U.S. application Ser. No. 13/811,483, which was filed on Dec. 2, 2015, and which is a U.S. National Stage entry of International Application No. PCT/GB2011/001102, which was filed on Jul. 22, 2011, and which claims the foreign priority benefit of British Application No. 1012333.9, which was filed on Jul. 22, 2010. The disclosures of those applications are incorporated by reference herein in their entireties.

The present invention is directed at fibres and in particular the use thereof in wound dressings for the reduction of the damaging activity of wound exudate components such as protein degrading enzymes and inflammatory mediators in wounds and a method of preparing the fibres. The fibres are used particularly for the binding, sequestering or inhibiting of damaging components present in a chronic wound environment. The fibres are preferably multi component fibres comprising pectin and more preferably pectin and gelatin.

The presence of inflammation-derived components, such as protein degrading enzymes (proteases), lipid mediators, and the like, in a wound environment can be detrimental, when in excess, to the progression of wound healing. There are two main classes of proteases, the matrix metalloproteinases (MMPs) and the elastases, which act in concert in order to be effective in breaking down body tissue. For example, the synthesis of new granulation tissue may be inhibited by elevated levels of enzymes which could impede the healing process. It has therefore been seen as desirable to reduce these elevated or excess levels of inflammation-derived components from the wound environment to enhance wound healing. Wound healing may be observed by visual improvement of the wound bed (new granulation tissue formation) and a reduction in wound size.

In the past, a number of wound dressings were proposed with the aim of modulating protease in a wound. These dressings include Promogran™ (Systagenix Wound Management), a lyophilized collagen-oxidised regenerated cellulose composition in the form of a matrix sheet that gels on contact with wound exudate. It is however targeted only at MMPs. Biostep™ (Smith & Nephew), a collagen matrix wound dressing composed of collagen, sodium alginate, carboxyl methylcellulose, and ethylenediaminetetraacetic acid (EDTA) is in the form of a matrix sheet dressing and is also targeted at MMPs. Tegaderm™ Matrix (3M) which has as its active ingredients a mixture of metal salts which are claimed to modulate MMPs is in the form of a matrix sheet. Besides specificity to MMPs, all these dressings have limited fluid handling capability in comparison to fibre based dressings and particularly those based on Hydrofiber® such as AQUACEL® (ConvaTec Inc).

In the art dressings are known that are either specific to one of the two major classes of proteinases known to be in chronic wounds and therefore are of limited effectiveness, or have limited fluid handling capability, or are dressing components in a form that presents practical difficulties, for example they are in powder form. Powders, if loose in the dressing, can fall out and need to be removed by irrigation of the wound. If contained in some kind of pocket in the dressing or used a separate pocketed component cannot be cut to fit the wound without encountering the problems of loose powder. US2002012693A discloses a dressing said to have protease-lowering activity which is composed of a support matrix onto which peptide elastase inhibitors are incorporated by covalent bonding. The composition is targeted at elastase only. US2006142242A discloses a phosphate starch composition said to have both elastase and MMP sequestering capability but typically used in the form of a powder.

Edwards et al (2007) "Human neutrophil elastase and collagenase sequestration with phosphorlyated cotton wound dressings" Cotton Chemistry Utilization, Journal of Biomedical Materials Research part A, also disclosed a phosphorylated cotton composition with elastase and MMP lowering capability but applied to a simple cotton gauze. WO07137733A and WO09068249A disclose a polyacrylate superabsorber (Paul Hartmann AG) said to have MMP inhibiting activity and good fluid handling capability but it appears to be active against MMPs only. Walker et al (2007) "In Vitro Studies to Show Sequestration of Matrix Metalloproteinases by Silver-Containing Wound Care Products" Ostomy Wound Management 2007; 53(9):18-25, discloses the ability of several wound care products including a silver-containing carboxymethyl cellulose (CMC) Hydrofiber® dressing (Aquacel Ag) to reduce MMPs in vitro.

It is therefore desirable to provide fibres able to reduce the damaging activity of a number wound exudate components, such as protein degrading enzymes and inflammatory mediators, in wounds and which either have inherent fluid management properties or can be processed into a wound dressing with suitable fluid management properties. Fibres based on pectin have now been made that are suitable for use in the treatment of wounds to alleviate the above problems.

Accordingly there is provided by the present invention multi component fibres for the reduction of the damaging activity of wound exudate components such as protein degrading enzymes and inflammatory mediators in wounds, the fibres comprising:

from 10% to 100% by weight of the fibres of pectin and a sacrificial proteinaceous material in a weight ratio of 100:0 to 10:90 pectin to sacrificial proteinaceous material and from 0% to 90% by weight of the fibres of another polysaccharide or a water soluble polymer.

Suitably the fibres are able to reduce the level of damaging enzyme activity compared to a control by at least 25%, more suitably by at least 50% and preferably by at least 75% when measured by the MMP method as described in Example 2 and at T=0.

There is further provided by the present invention multi component pectin fibres capable of reducing the level of damaging enzyme activity in vitro by at least 25% when measured by the MMP method as described in Example 2 at T=0.

The fibres may comprise a sacrificial proteinaceous material such as gelatin, collagen, globular protein such as whey, soy and milk protein, albumin or casein. The function of sacrificial proteinaceous material when present is to maximally occupy the catalytic activities of the proteinases thereby reducing the proteinase activity against body proteins. Preferably the sacrificial proteinaceous material is gelatin.

To improve the structural integrity of the fibres, they may comprise another polysaccharide such as alginate, chitosan or its derivatives or derivatives of cellulose, guar gum, xanthan gum, locust bean gum, dextrin, agar-agar, cellulose gum or other starch based material and to improve the fluid handling capabilities the fibres may comprise a water soluble polymer such as polyacrylate, polyester or polyamide. To improve the antibacterial function of the fibres they may comprise silver, gold and platinum or salts thereof and/or chelating agents such as EDTA or citric acid. The fibres may also comprise divalent ions such as calcium or zinc, magnesium, copper or iron and buffering agents or a humectant or surfactant to improve textiling such as polysorbate.

Preferably the fibres comprise from 75% to 100% by weight of the fibres or more preferably 90% to 100% of pectin and a sacrificial proteinaceous material in a weight ratio of 100:0 to 10:90 pectin to sacrificial proteinaceous material. Preferably the weight ratio of pectin to sacrificial proteinaceous material in the fibres is from 90:10 to 10:90, more preferably 90:10 to 30:70, or 80:20 to 50:50 and more preferably 70:30.

In a second aspect of the present invention there is a wound dressing comprising multi component pectin fibres for use in the reduction of the damaging activity of wound exudate components such as protein degrading enzymes and inflammatory mediators in wounds.

The wound dressings of the present invention may comprise other fibres in addition to the multi component pectin fibres such as cellulose or cellulose derivative fibres. The fibres may be present as a homogenous blend of multi component fibres with textile or gel forming fibres or may be present as a discrete layer in a wound dressing construct. The dressing may comprise from 10% to 100% by weight of multi component pectin fibres with 0% to 90% by weight of another gel forming fibre such as CMC fibre. Preferably the dressing may comprise from 25% to 75% by weight of multi component pectin fibres with 25% to 75% by weight of another gel forming fibre, more preferably the dressing comprises a 50% to 50% blend.

Multi component pectin fibres suitable for use according to the present invention can be prepared by the following steps:
(i) Adding pectin and gelatin to water to form a dope;
(ii) Forcing the dope through a spinneret;
(iii) Crosslinking with a source of ions to form fibres and
(iv) Drying the fibres Preferably, the dope solution is prepared at a concentration from 2 to 11% (w/v) by dissolving pectin in hot water (40-80° C.) until a homogenous opaque mixture is obtained followed by cooling to room temperature and resting to stabilise the viscosity and remove air bubbles. Spinning to form the fibres may be done by conventional wet spinning which includes passing the dope through a spinneret into a coagulation bath which can be composed of divalent metal ions such as calcium chloride or zinc chloride at a concentration from 0.5 to 35% (w/v). Next, the obtained pectin fibres may be washed and stretched in a water bath. The fibres may be rinsed in a water miscible non-aqueous solvent such as acetone, IDA, isopropyl alcohol or propan-2-ol to remove any residual water from the fibre core and facilitate drying, followed by a drying step at a temperature generally below 120° C.

Alternatively electrospinning may be used to produce nanofibres for example fibres having a diameter of a few hundred nanometers.

Pectin suitable for use in the fibres or the preparation of fibres according to the invention is preferably either low methoxy pectins with methoxyl content lower than 15%, or amidated pectin with a degree of esterification in a range from 10 to 30% and a degree of amidation comprised between 10 and 30%. The molecular weight of these pectins is preferably in a range of 30,000 and 85,000 daltons so as to optimise the required viscosity of the dope solution and the tensile strength properties of the fibres. Suitable pectin is that available commercially as GENU Pectin Type LM-104 AS-FS ex CP Kelco which is a pectin stabilised with sugar.

Gelatin for use in the fibres or the preparation of fibres according to the invention is preferably of Type A gelatin. Suitable gelatin is that available commercially as porcine Gelatin powder ex PB Leiner.

As used herein the term fibre means both relatively short, discrete, randomly oriented material (sometimes known as staple fibre) and yarns made therefrom (sometimes known as staple yarn) and relatively long, structured, continuous filament yarn or continuous filament fibre. The fibres may have a staple length of 5 mm to 70 mm, usually 20 mm to 50 mm. The fibres may have a diameter in the nanometre to millimetre range.

The invention is illustrated by the following drawings in which FIG. 1 shows the MMP activity of various fibres and their components.

The invention is further illustrated in the following examples:

EXAMPLE 1

Multi component fibres according to the invention were prepared as follows.

9 litres of 8% (w/v) gelatin:pectin (30:70) dope solution were prepared. 216 g of gelatin powder was slowly added under stirring and homogenising in deionised water previously heated at 40° C. The solution was left to mix by a scraper and a homogeniser during 30 minutes at 40° C. Then, 504 g of pectin powder was slowly added using the same method as the gelatin and the mixture was left to stir and homogenize for a further 30 minutes. When the solution was homogeneous, the stirring was stopped and vacuum was applied to the solution for 5 minutes at about 0.2 bar pressure in order to remove excess air from the mixture. The solution was left to cool and settle for about 24 hours.

The dope solution was transferred in a 3 litre kier pressurized at 5 Psi. The spinning was carried out at room temperature. Directly after the kier, the dope solution was pushed through a candle filter composed of viscose cloth. Then, the dope solution was pushed through a flexible hose to a mesh filter mounted in the spinneret before going through the spinneret. The spinneret had 500 holes of 75 □m diameter and the pump flow rate was set to 70 L/hour over three spinnerets of 40,000 holes each with a hole diameter of 75 □m. The spin bath was a 10 litre bath of 5% (w/v) calcium chloride dehydrate in deionised water for the first run and a 10 litres bath of 5% (w/v) zinc chloride in deionised water for the second run. After leaving the coagulation bath, the formed filaments went through four different wash baths; each bath had a capacity of 10 litres. The first wash bath was a water bath where a draw ratio of 1:6 was applied, followed by a 25% (v/v) aqueous IDA (Industrial Denatured Alcohol) bath. The third wash bath was filled by a 50% (v/v) IDA aqueous solution and the fourth bath was a 75% (v/v) IDA aqueous bath. The final bath was 100% IDA in which the fibres were left for about 1 hour before being removed, squeezed by hand and dried in a fan oven at 40 C. The baths were separated by godets which lead the filaments through the following baths and applied a stretch to the filaments. A draw ratio of 1.6 was targeted between the first godet (exit of the coagulation bath) and the second bath.

Both spinning runs into calcium and into zinc provided filaments that were soft and strong enough to be processed into wound dressings. The fibres were physically comparable to other fibres used in wound dressings in terms of strength and diameter. Tables 1 and 2 show details of strength measured by BSEN ISO 5079, 1996 and diameter measured by SEM and image analysis tool.

TABLE 1

Fibre strength

| Sample | Average Max Force (cN/fibre) | Average Extension (%) |
|---|---|---|
| Fibres spun into $CaCl_2$ | 3.1 (3.6) | 9.0 (4.7) |
| Fibres spun into $ZnCl_2$ | 4.0 (2.6) | 12.6 (5.1) |
| Hydrofibre tow fibres | 5.9 (2.8) | 10.0 (2.9) |
| Alginate tow fibres | 4.6 (0.9) | 11.8 (4.6) |

Note:
Numbers in brackets are the standard deviations.

TABLE 2

Fibre diameter

| Sample | Average Fibre Diameter (micron) | Standard Deviation |
|---|---|---|
| Fibres spun into $CaCl_2$ | 12.44 | 1.13 |
| Fibres spun into $ZnCl_2$ | 15.66 | 1.73 |
| Hydrofibre tow fibres | 11.56 | 0.66 |
| Alginate tow fibres | 15.60 | 4.22 |

EXAMPLE 2

This example shows the proteinase uptake of the fibres.
MMP Method

Nine milligram samples of the various fibres were placed in 7 ml vials and to these samples 40 μl of pre-prepared MMP solution was added. These samples were left to stand for 2-3 minutes to ensure that the enzyme was completely taken up by the material. To these hydrated samples 960 μl of MMP assay reaction buffer was added and the sample were mixed gently by hand. After a further 2-3 minutes 2×90 μl samples were removed from the vials and transferred to individual wells of a multiwell plate for later analysis ($T_0$). The vials containing the samples were left to stand for 2 hours at room temperature after which a further 2×90 μl samples were removed and processed as above ($T_{120}$).

Twenty microlitres of pre-prepared DQ gelatin was added to each well of the multiplate plate ($T_0$ and $T_{120}$ plates) and the change in levels of fluorescence was measured over a period of approximately 30 minutes using a Tecan F200 multiwell plate spectrophotometer. The percentage reduction in MMP activity present in the sample-containing vials was calculated from the level of fluorescence detected.

Appropriate positive and negative controls as well as blank samples were prepared and run in parallel.

The level of MMP activity at the T=0 time point for all four runs of the multi component fibre is roughly comparable with that of Aquacel®. However an improvement is observed for the T=120 minute time point particularly in those fibres containing zinc. This suggests that the effect of MMP modulation is longer lasting in the fibres of the invention. Reduction in MMP activity is superior to CMC tow and Kaltostat tow at both time points. The results are shown in Table 3 (FIG. 1)

These results show the broad spectrum reduction of damaging activity of wound exudate components provided by the fibres of this invention.

EXAMPLE 3

Fibres manufactured with the method of Example 1 were observed under environmental scanning electron microscopy to investigate their gelling properties. The fibres were found to demonstrate moderate swelling and gelling, with some areas blending in during the hydration phase. The swelling ratio for the fibres spun into CaC12 is higher, at 2.3, than that of fibres sun into ZnC12 (1.54).

EXAMPLE 4

Fibres manufactured with the method of Example 1 were processed into a textile form. The fibres were cut into staple lengths of 55 mm, opened manually using hand cards and carded using a pilot scale card of 500 mm working width. They were then needle punched into a textile web, with the characteristics given in Table 5. The weight per unit area was measured gravimetrically by weighing a know size of sample. The moisture regain was measured gravimetrically, after a minimum of 24 hours conditioning at 20±2° C.± and 65±4% RH, and after drying for 4 hours at 105° C. in a fan oven.

TABLE 5

Physical characteristics of 100% pectin/gelatin textile samples

| | Textile sample from fibres spun in $CaCl_2$ | Textile sample from fibres spun in $ZnCl_2$ |
|---|---|---|
| Weight per unit area | Sample 1: 34.20 gsm<br>Sample 2: 119.20 gsm | 269.07 gsm |
| Moisture regain | Sample 2: 18.9% | 18.4% |
| Thickness | Sample 1: 1.27 mm<br>Sample 2: 3.69 mm | 5.05 mm |

The absorbency and retention of the textile samples manufactured using the fibres spun into zinc chloride were measured using a BP recommended physiological solution as a hydrating medium. Absorbency is measured by weighing a known size of sample (typically 5 cm×5 cm), hydrating with 20 times its weight in the hydrating medium, incubating at 37° C. for 30 minutes, draining off excessive fluid by holding the sample with forceps for 30 seconds, and weighing the hydrated and drained sample. Retention is measured by applying the weight equivalent to 40 mmHg to the hydrated and drained sample after it has been weighed, leaving for 1 minute and re-weighing. To assess further the fluid management capabilities, the ability of the material to prevent lateral spread was also evaluated. This was done by immersing a 1.5 cm wide strip by 1 cm (along a marked line) into a BP recommended physiological solution (solution A) containing Eosin dye for 1 minute. After the minute, the sample is removed and the distance of fluid movement from the marked line is measured. The absorbency, retention and lateral wicking of the material produced are given in Table 6.

TABLE 6

Fluid management properties of 100% pectin/gelatin textile samples

| | Textile sample from fibres spun in $ZnCl_2$ |
|---|---|
| Absorbency per weight of sample | 11.5 g/g |
| Absorbency per area of sample | 0.325 g/cm² |

TABLE 6-continued

Fluid management properties of 100% pectin/gelatin textile samples

|  | Textile sample from fibres spun in ZnCl$_2$ |
|---|---|
| Retention per weight of sample | 6.0 g/g |
| Retention per area of sample | 0.170 g/cm$^2$ |
| Lateral wicking in the machine direction | 3.7 cm |
| Lateral wicking in the transverse direction | 3.6 cm |

EXAMPLE 5

Fibres manufactured with the method of Example 1 were processed into a textile form in a 50% blend with Hydrofibre tow material, using a similar route as described in Example 4. The physical characteristics, and fluid handling characteristics, measured as per Example 4, are given in Table 7.

TABLE 7

Physical and fluid handling characteristics of 50% blended fibres

|  | 50% Blended textile sample from fibres spun in CaCl$_2$ | 50% Blended textile sample from fibres spun in ZnCl$_2$ |
|---|---|---|
| Weight per unit area | 160.5 gsm | 134.1 gsm |
| Moisture regain | 17.3% | 16.8% |
| Thickness | 5.05 mm | 4.68 mm |
| Absorbency per weight of sample | 17.7 g/g | 14.5 g/g |
| Absorbency per area of sample | 0.271 g/cm$^2$ | 0.248 g/cm$^2$ |
| Retention per weight of sample | 9.3 g/g | 7.9 g/g |
| Retention per area of sample | 0.151 g/cm$^2$ | 0.135 g/cm$^2$ |
| Lateral wicking in the machine direction | 1.5 cm | 1.9 cm |
| Lateral wicking in the transverse direction | 1.5 cm | 1.7 cm |

These results show the advantage of the fibres according to the invention which can be processed along with conventional dressing fibres to give a dressing having the combined advantages of good fluid handling characteristics and the reduction of damaging activity of wound components.

EXAMPLE 6

Multi component fibres according to the invention were manufactured in a wet spinning process similar to that described in Example 1 but on a smaller scale. The fibres had a range of ratios of components as shown below.

| Ratio | Fibre Component |
|---|---|
| 10:90 | Gelatin:Pectin |
| 15:70:15 | Gelatin:Pectin:CMC powder |
| 15:70:15 | Gelatin:Pectin:Alginate |

Preparation of Dope Solutions:

300 ml of 8% solids solutions were prepared for each component by heating 288 ml of deionized water to 40 C on a stirrer hot plate. The gelatin was added slowly with stirring and once fully integrated the other components were added, pectin being added last. The whole was slowly mixed and homogenised until the solids had all dissolved and the solutions were left to cool overnight.

Matrix of Weights Required (g)

| Gelatin | Pectin | Alginate | CMC | DI Water |
|---|---|---|---|---|
| 2.4 | 21.6 | — | — | 288 ml |
| 3.6 | 16.8 | — | 3.6 | 288 ml |
| 3.6 | 16.8 | 3.6 | — | 288 ml |

Wet Spin Method

The dope solution was pumped using a peristaltic pump at low flow rate (2.25 ml/min) to a spinneret which spun fibres into a 5% calcium chloride coagulation bath. The fibres were collected in a bath of 50:50 IDA:water. They were then washed in 100% IDA before being air dried in a fume hood.

All spinning runs provided filaments that were soft and strong enough to be processed into wound dressings.

EXAMPLE 7

In this example the capability of multicomponent fibres according to the invention to be formed into wound dressing was assessed along with the physical properties of the resulting dressing. A medium scale spinning rig was used to produce 80 g of each type of fibre tow. The fibres were spun into either a calcium chloride bath or a zinc chloride bath. The resulting tow was opened, carded and needled in order to produce a non-woven fabric. From each tow, two non woven pads were produced, one with 100% fibres according to the invention and one with 50% fibre according to the invention and 50% of Hydrofibre® a carboxymethyl cellulose fibre produced from Lyocell and available in the product Aquacel (ex ConvaTec). The resulting pads were irradiated to evaluate any change in key physical properties.

Wet Spinning: The wet spinning process was the same as that used in Example 1. Once the fibres had been washed they were cut, tied at one end and placed in a bath containing 100% IDA for 1 hour. The fibres were then squeezed and placed in an oven at 40 C for an hour until dry.

Observations: The fibres spun well into the calcium chloride coagulation bath and the fibres once dry were very soft, easily separated and were white/cream in colour. Some problems were experienced with the zinc coagulation bath in that some of the zinc precipitated out of the solution and there was some slackness in the fibre as it emerged from the spinneret. Fibres were produced however, which were soft and off white/slightly tan in colour.

Textiling of the Fibres: The dried fibres were cut to 55 mm and opened manually using hand cards. They were carded using a pilot scale Automatex Model CA500 card with a 500 mm working width, single swift, 3 pairs of workers and strippers and a single fancy roller. Four carded webs were produced.

Needling: Needling was conducted on a pilot scale Garnett/Bywater Needleloom.

The webs were folded either two or four fold to provide more bulk during needling.

The resulting products were referenced as follows:
HF-2010/078-2: 100% Biointeractive fibres spun into CaCl2 2$n^d$ trial (folded 4 times)
HF-2010/079: 100% Biointeractive fibres spun into ZnC12 (folded 4 times)
HF-2010/080: 50% Biointeractive fibres spun into CaCl2 with 50% Hydrofiber® (folded twice only)
HF-2010/081: 50% Biointeractive fibres spun into ZnC12 with 50% Hydrofiber® (folded twice only)

Irradiation: The samples were gamma irradiated with a dose between 25-42 kGy.
Absorption

SUMMARY

The absorbency of the non woven (CaCl2) material, in its unblended and blended form, is comparable (on a weight per weight basis), to AQUACEL. The absorbency of the samples spun into ZnC12 is slightly lower in general. There is little difference between irradiated and non-irradiated samples. The table below provides the absorbency results expressed in g/g.

|  | H F-201 0/078-2 100% Biointer-active fibres spun into CaCl$_2$ | H F-20 10/079 100% Biointer-active fibres spun into ZnCl$_2$ | H F-201 0/080 50% blend Biointer-active fibres spun into CaCl$_2$ | H F-20 10/081 50% blend Biointer-active fibres spun into ZnCl$_2$ |
|---|---|---|---|---|
| Non-irradiated | N/A | 11.5 (0.5) | 17.7 (3.7) | 14.5 (0.5) |
| Irradiated | 17.2 (1.2) | 11.7 (0.7) | 18.0 (0.9) | 15.0 (0.2) |

Retention

Summary

The blended fibres have slightly better retention than the pure multicomponent fibres, and overall, retention appears to be lower than AQUACEL®. The results also indicate that irradiation results in a small drop in retention. The table below provides the retention results expressed as g/g.

|  | H F-201 0/078-2 100% Biointer-active fibres spun into CaCl$_2$ | H F-20 10/079 100% Biointer-active fibres spun into ZnCl$_2$ | H F-201 0/080 50% blend Biointer-active fibres spun into CaCl$_2$ | H F-20 10/081 50% blend Biointer-active fibres spun into ZnCl$_2$ |
|---|---|---|---|---|
| Non-irradiated | N/A | 6.0 (0.2) | 9.3 (0.3) | 7.9 (0.2) |
| Irradiated | 5.8 (0.4) | 4.9 (0.6) | 7.6 (0.3) | 7.0 (0.2) |

This example has provided the proof of principle that the calcium- and zinc-spun fibres according to the invention can be manufactured into a textile form, with attractive fluid management properties. The trial has confirmed that the fibres according to the invention are strong enough to be successfully manufactured into a non woven either as a 100% material or as a blended material with Hydrofiber®.

The fibres that were spun into a bath containing calcium ions were more easily textiled than fibres spun into zinc ions.

EXAMPLE 8

The dressings produced in Example 7 were sprayed with silver and irradiated using the following method.

Each dressing was passed through an ultrasonic spray of silver nitrate (5%) aqueous solution followed by an ultrasonic spray of sodium chloride (3%) aqueous solution. The dressing was exposed first to the silver solution for approximately 10 seconds then to the salt solution for approximately 10 seconds. The resulting dressing was dried using a forced air dryer for approximately 1 minute.

The dressings were each irradiated using gamma irradiation at a dose of 31.4 kGy. All samples were visually equivalent once irradiated to those prior to irradiation.

EXAMPLE 9

To assess the ability of the dressings of Example 7 to modulate elastase a fluorescence assay was performed and data reported as activity of elastase remaining in the supernatant as a percentage of the positive control.

Testing was performed using an EnzCheck Elastase Assay kit following this method. Nine milligram samples of the various fibres were placed in 7 ml vials and to these samples 40 µl of pre-prepared elastase solution was added. These samples were left to stand for 2-3 minutes to ensure that the enzyme was completely taken up by the material. To these hydrated samples 960 µl of elastase assay reaction buffer was added and the sample were mixed gently by hand to ensure. After a further 2-3 minutes 2×20 µl samples were removed from the vials and transferred to individual wells of a multi-well plate for later analysis ($T_0$). The vials containing the samples were left to stand for 2 hours at room temperature after which a further 2×20 µl samples were removed and processed as above ($T_{10}$). Ninety microlitres of elastase assay reaction buffer was added to each well of the multiwell plate to bring the final volume to 110 µl.

Forty microlitres of pre-prepared DQ elastin was added to each well of the multiplate plate ($T_0$ and $T_{120}$ plates) and the change in levels of fluorescence was measured over a period of approximately 30 minutes using a Tecan F200 multiwell plate spectrophotometer. The percentage reduction in elastase activity present in the sample-containing vials was calculated from the level of fluorescence detected.

Appropriate positive and negative controls as well as blank samples were prepared and run in parallel. This therefore shows the dressings ability to modulate elastase activity.

| Sample | % remaining activity at $T_0$ | Standard Deviation | % remaining activity at $T_{120}$ | Standard Deviation |
|---|---|---|---|---|
| Negative | 6.2 | 9.42 | −23.1 | 28.7 |
| HF2010/078 | 7.9 | 5.29 | 6.5 | 12.66 |
| HF2010/079 | 15.4 | 12.3 | 42.6 | 6.44 |
| HF2010/080 | 9.2 | 5.82 | −8.0 | 15.88 |
| HF2010/081 | 16.4 | 0.46 | 13.2 | 20.14 |

All of the dressings according to the invention perform well both initially and over two hours with the highest elastase level returning to 40% when testing HF2010/079. Dressing HF2010/078 performs best overall with approximately 90% reduction at $T_0$ and $T_{120}$. Overall calcium containing materials perform better over the course of the assay.

To assess the ability of the dressings to modulate MMP, a fluorescence assay was performed and data reported as activity of MMP remaining in the supernatant as a percentage of the positive control. The method followed was that of Example 2 which gave the following results:

| Sample | % remaining activity at $T_0$ | Standard Deviation | % remaining activity at $T_{120}$ | Standard Deviation |
|---|---|---|---|---|
| Negative | 1.2 | 0.18 | 1.2 | 1.2 |
| HF2010/078 | 4.5 | 2.75 | 69.7 | 9.36 |
| HF2010/079 | 5.4 | 1.74 | 9.9 | 4.64 |
| HF2010/080 | 3.8 | 1.61 | 90.3 | 10.6 |
| HF2010/081 | 1.8 | 0.16 | 11.9 | 3.77 |

EXAMPLE 10

In this example, nanoscale fibres were prepared from solutions of gelatin and pectin. The optimum conditions centre on a solids concentration of 25 w/w % with gelatin to pectin ratios between 90/10 and 70/30 with a needle to collector distance of 10 cm and a voltage of 20 kV.

Solutions for electrospinning were prepared in the following manner: A volume of 10 ml of distilled water was measured out by weight and heated to a temperature of 45° C. (±3° C.) using a hot plate. The temperature of the water was periodically measured. The appropriate amount of gelatin and pectin were measured out by weight. Gelatin was dissolved in the water by adding small amounts of gelatin into the water at a time. The solution was agitated using a laboratory mixer with a rotation speed of 550 rpm (±50 rpm) until each amount dissolved. When the entire amount of gelatin was fully dissolved the pectin was added in the same manner. After dissolving the components, the solution was weighed and water added if evaporation had occurred. This ensured the final solution was at the specified concentration. When all the material was fully dissolved and mixed the solution was allowed to cool to room temperature before electrospinning. Solutions not in use were stored in a laboratory refrigerator at −5° C.

The electrospinning equipment consisted of a high voltage power supply, syringe pump and a grounded collector. Solutions were loaded into a 5 ml Luer lock glass syringe fitted with a 22 G needle which has an internal diameter of 0.41 mm and a needle length of 12 mm. The syringe was mounted in a syringe pump, with flow rates from 0.1 ml/min-1 ml/min. The syringe pump was used in a standard room temperature environment, or housed inside a temperature controlled enclosure box The high voltage was provided by a Glassman High Voltage Unit (0-30 kV) with respect to ground. The voltage was measured on the needle using a high voltage probe and multi-meter. Samples are collected onto a flat electrode formed from aluminium foil.

The results indicate that electrospinning a combination of gelatin/pectin is possible at a total solid concentration between 15% wt and 30% wt at a gelatin to pectin ratio of 90/10 at elevated temperatures. Spinning solutions with a gelatin/pectin ratio of 70/30 was possible at concentrations of 15% wt-25% wt. As the solution viscosity increased with increasing concentration or increasing pectin to gelatin ratio, higher voltages above 15 kV were employed in order to allow the electrospinning process to occur.

The invention claimed is:

1. A method of preparing multi-component pectin fibres, the method comprising:
   adding pectin and a sacrificial proteinaceous material to water to form a dope;
   forcing the dope through a spinneret;
   crosslinking the dope with a source of ions to form fibres; and
   drying the fibres,
   wherein adding pectin and the sacrificial proteinaceous material to water to form the dope comprises:
   adding the sacrificial proteinaceous material to heated water;
   mixing the sacrificial proteinaceous material and the heated water while heating the sacrificial proteinaceous material and the heated water to form a mixture;
   adding pectin to the mixture while heating the mixture to form a homogeneous solution;
   applying a vacuum to the homogeneous solution to remove excess air; and
   cooling the homogeneous solution to obtain the dope such that the dope is at room temperature before forcing the dope through the spinneret, and
   wherein the multi-component pectin fibres comprise:
   a first fibre component consisting of pectin and gelatin;
   a second fibre component consisting of gelatin, pectin, and carboxymethyl cellulose fibre; and
   a third fibre component consisting of gelatin, pectin, and alginate.

2. The method of claim 1, wherein the sacrificial proteinaceous material is gelatin.

3. A method of preparing multi-component pectin fibres, the method comprising:
   adding pectin and a sacrificial proteinaceous material to water to form a dope; and
   forcing the dope through a spinneret while inducing a voltage between the spinneret and a collector plate in a temperature controlled environment,
   wherein adding pectin and the sacrificial proteinaceous material to water to form the dope comprises:
   adding the sacrificial proteinaceous material to heated water;
   agitating the sacrificial proteinaceous material and the heated water using a mixer to form a mixture in which the sacrificial proteinaceous material is fully dissolved;
   adding pectin to the mixture to form a solution;
   agitating the solution until the pectin is fully dissolved; and
   cooling the solution to obtain the dope such that the dope is at room temperature before forcing the dope through the spinneret, and
   wherein the multi-component pectin fibres comprise:
   a first fibre component consisting of pectin and gelatin;
   a second fibre component consisting of gelatin, pectin, and carboxymethyl cellulose fibre; and
   a third fibre component consisting of gelatin, pectin, and alginate.

4. The method of claim 1, wherein forcing the dope through the spinneret comprises:
   passing the dope through a first filter;
   filtering the dope passed through the first filter using a second filter mounted in the spinneret; and
   processing the dope filtered by the second filter using the spinneret.

5. The method of claim 4, wherein crosslinking the dope with the source of ions to form fibres comprises:

crosslinking the dope with a source of calcium ions during a first spinning operation performed in the spinneret;

crosslinking the dope with a source of zinc ions during a second spinning operation performed in the spinneret subsequent to the first spinning operation to form fibres.

6. The method of claim 5, further comprising:

washing the fibres in water in a first wash bath;

washing the fibres in a second wash bath containing a water miscible solvent in a first concentration subsequent to washing the fibres in the first wash bath;

washing the fibres in a third wash bath containing a water miscible solvent in a second concentration higher than the first concentration subsequent to washing the fibres in the second wash bath;

washing the fibres in a fourth wash bath containing a water miscible solvent in a third concentration higher than second concentration subsequent to washing the fibres in the third wash bash; and washing the fibres in a final wash bath containing a water miscible solvent in a fourth concentration higher than the third concentration subsequent to washing the fibres in the fourth wash bath.

7. The method of claim 1, wherein the fibres comprise:

from 10% to 100% by weight of the fibres of pectin and the sacrificial proteinaceous material in a weight ratio of 90:10 to 10:90 pectin to sacrificial proteinaceous material;

from 0% to 90% by weight of the fibres of another polysaccharide or a water soluble polymer; and a divalent ion, wherein the pectin and the sacrificial proteinaceous material are crosslinked with the divalent ion to form the fibres suitable for processing into wound dressings capable of absorbing wound exudate.

8. The method of claim 7, wherein:

the pectin is low methoxy pectin with a methoxyl content lower than 15% or amidated pectin with a degree of esterification in a range from 10% to 30% and a degree of amidation in a range from 10% to 30%; and the sacrificial proteinaceous material is selected from gelatin, collagen, whey, soy, casein, or albumin.

9. The method of claim 7, wherein the fibres comprise from greater than 0% to 90% by weight of carboxymethyl cellulose fibre.

10. The method of claim 3, wherein the fibres comprise:

from 10% to 100% by weight of the fibres of pectin and the sacrificial proteinaceous material in a weight ratio of 90:10 to 10:90 pectin to sacrificial proteinaceous material;

from 0% to 90% by weight of the fibres of another polysaccharide or a water soluble polymer; and a divalent ion, wherein the pectin and the sacrificial proteinaceous material are crosslinked with the divalent ion to form the fibres suitable for processing into wound dressings capable of absorbing wound exudate.

11. The method of claim 3, wherein forcing the dope through the spinneret while inducing the voltage between the spinneret and the collector plate in the temperature controlled environment comprises electrospinning the dope using a high voltage power supply configured to supply a voltage of up to 30 kV, a syringe pump, and the collector plate to obtain the multi-component pectin fibres.

12. The method of claim 11, wherein:

a collector distance between the collector plate and a needle fitted to a syringe mounted in the syringe pump is at least 10 cm.

13. A method of preparing multi-component pectin fibres, the method comprising:

preparing a first fibre component solution comprising pectin and a sacrificial proteinaceous material;

preparing a second fibre component solution comprising pectin, the sacrificial proteinaceous material, and carboxymethyl cellulose fibre;

preparing a third fibre component solution comprising pectin, the sacrificial proteinaceous material, and alginate;

mixing the first fibre component solution, the second fibre component solution, and the third fibre component solution to form a dope;

forcing the dope through a spinneret; and crosslinking the dope with a source of divalent ions to form fibres, wherein the multi-component pectin fibres comprise:

a first fibre component consisting of pectin and gelatin;

a second fibre component consisting of gelatin, pectin, and carboxymethyl cellulose fibre; and a third fibre component consisting of gelatin, pectin, and alginate.

14. The method of claim 13, wherein preparing the first fibre component solution comprises:

adding the sacrificial proteinaceous material to heated water;

mixing the sacrificial proteinaceous material and the heated water to form a mixture; and adding pectin to the mixture.

15. The method of claim 14, wherein preparing the second fibre component solution comprises:

adding the sacrificial proteinaceous material to heated water;

mixing the sacrificial proteinaceous material and the heated water to form a mixture;

adding carboxymethyl cellulose fibre to the mixture; and adding pectin to the mixture subsequent to adding carboxymethyl cellulose fibre to the mixture.

16. The method of claim 15, wherein preparing the third fibre component solution comprises:

adding the sacrificial proteinaceous material to heated water;

mixing the sacrificial proteinaceous material and the heated water to form a mixture;

adding alginate to the mixture; and adding pectin to the mixture subsequent to adding alginate to the mixture.

17. The method of claim 16, wherein crosslinking the dope with the source of divalent ions comprises crosslinking the dope with a source of calcium ions during a spinning operation performed in the spinneret, and wherein the method further comprises:

washing the fibres in a first wash bath containing a water miscible solvent in a first concentration; and washing the fibres in a second wash bath containing a water miscible solvent in a second concentration higher than the first concentration subsequent to washing the fibres in the first wash bath.

18. The method of claim 13, wherein:

the first fibre component consists of pectin and gelatin in a weight ratio of 90:10;

the second fibre component consists of gelatin, pectin, and carboxymethyl cellulose fibre in a weight ratio of 15:70:15; and the third fibre component consists of gelatin, pectin, and alginate in a weight ratio of 15:70:15.

* * * * *